United States Patent
Franko et al.

(10) Patent No.: US 10,995,346 B2
(45) Date of Patent: May 4, 2021

(54) SYSTEM AND PROCESS FOR ADDING PRE-FERMENTATION SEPARATED NON-FERMENTABLES TO A POST-FERMENTATION STREAM

(71) Applicant: Fluid Quip Technologies, LLC, Springfield, OH (US)

(72) Inventors: Michael Franko, Denver, CO (US); John Kwik, Bellbrook, OH (US); Neal Jakel, Cedar Rapids, IA (US)

(73) Assignee: Fluid Quip Technologies, LLC, Springfield, OH (US)

( * ) Notice: Subject to any disclaimer, the term of this patent is extended or adjusted under 35 U.S.C. 154(b) by 378 days.

(21) Appl. No.: 15/649,806

(22) Filed: Jul. 14, 2017

(65) Prior Publication Data

US 2018/0016602 A1    Jan. 18, 2018

Related U.S. Application Data

(60) Provisional application No. 62/362,334, filed on Jul. 14, 2016.

(51) Int. Cl.

| | |
|---|---|
| *C12P 7/14* | (2006.01) |
| *C12P 7/08* | (2006.01) |
| *C12P 7/10* | (2006.01) |
| *C12P 7/64* | (2006.01) |
| *C12P 19/02* | (2006.01) |
| *C12P 7/40* | (2006.01) |
| *C12P 7/04* | (2006.01) |
| *C12P 7/00* | (2006.01) |

(52) U.S. Cl.
CPC ....... *C12P 7/14* (2013.01); *C12P 7/04* (2013.01); *C12P 7/08* (2013.01); *C12P 7/10* (2013.01); *C12P 7/40* (2013.01); *C12P 7/649* (2013.01); *C12P 19/02* (2013.01); *C12P 7/00* (2013.01); *Y02E 50/10* (2013.01)

(58) Field of Classification Search
CPC ............. C12P 7/14; C12P 7/06; C12P 19/16
See application file for complete search history.

(56) References Cited

U.S. PATENT DOCUMENTS

| | | | | |
|---|---|---|---|---|
| 9,012,191 | B2* | 4/2015 | Lee | C12M 21/12 435/161 |
| 9,029,126 | B2* | 5/2015 | Bleyer | C12P 7/06 435/262 |
| 2014/0065685 | A1* | 3/2014 | Rosenberger | C12P 7/14 435/162 |

OTHER PUBLICATIONS

Cheng et al. "Lactic acid production from enzyme-thinned corn starch using Lactobacillus amylovorus" Journal of Industrial Microbiology, 7 (1991) 27-34 (Year: 1991).*
Kvaalen et al. "Alcohol Distillation: Basic Principles, Equipment, Performance Relationships, and Safety" AE-117 Purdue University Cooperative Extension Service, Available online Aug. 2009, 24 pages (Year: 2009).*

* cited by examiner

*Primary Examiner* — Thane Underdahl
(74) *Attorney, Agent, or Firm* — Wood Herron & Evans LLP

(57) ABSTRACT

A system and process is disclosed for adding pre-fermentation separated non-fermentables, e.g., fiber, germ/oil, and/or protein, to a post-fermentation stream in a corn (or similar carbohydrate-containing grain) dry milling process for making alcohol and/or other biofuels/biochemical. The process includes mixing grain particles with a liquid to produce a slurry having starch and non-fermentables. The slurry is subjected to liquefaction to convert the starch in the slurry to complex sugars and produce a liquefied stream including the complex sugars and non-fermentables. After liquefaction but prior to fermentation of simple sugars resulting from conversion of the complex sugars, the non-fermentables are separated out to define a non-fermentables portion and an aqueous solution including the complex and/or simple sugars. The simple sugars are fermented to provide a fermented stream. Then, the separated non-fermentables portion is reincorporated back into the process into a post-fermentation stream. In one example, the non-fermentables may be mainly fiber.

12 Claims, 4 Drawing Sheets

US 10,995,346 B2

SYSTEM AND PROCESS FOR ADDING PRE-FERMENTATION SEPARATED NON-FERMENTABLES TO A POST-FERMENTATION STREAM

TECHNICAL FIELD

The present invention relates generally to corn dry milling, and more specifically, to a system and process for adding pre-fermentation separated non-fermentables to a post-fermentation stream in a corn (or similar carbohydrate-containing grain) dry milling process for making alcohol, such as ethanol, and/or other biofuels/biochemicals.

BACKGROUND

The majority of fuel alcohol (i.e., ethanol) in the United States is produced from No. 2 Yellow Dent Feed Corn. The most common method of production is the dry grind ethanol process, which is illustrated in FIG. 1. Traditionally, in the corn dry grind ethanol industry, all of the incoming corn components are eventually fermented and distilled together to produce alcohol even though the starch that is converted to sugar is the only corn component required for alcohol production. The main components of the corn kernel include starch, fiber, protein, and germ (oil). The starch component of the kernel is converted to simple sugars, which are used to feed alcohol-producing yeast, but all of the kernel components are processed together for process simplicity and yields. In most cases, the non-starch solids (or non-fermentables) are all recovered together after fermentation and distillation and are dried as distillers dried grains with solubles (DDGS), which also includes the spent yeast that was added to fermentation to produce the alcohol.

Recent technology developments have made pre-fermentation separation of non-starch grain components/solids more efficient and feasible. These technologies, like the system and process illustrated in FIG. 2, focus on separating out non-fermentables before full conversion of the starch to sugar and the fermentation of the starch/sugar component. This can be advantageous for the value of the co-products and also to increase fermenter capacity and efficiency. The separated non-fermentables require additional front end equipment for dewatering and/or drying the separated non-fermentables independent of the traditional stillage after fermentation and distillation, which increases the cost and complexity of the dry grind ethanol process.

It would thus be beneficial to provide an improved system and process for separating non-fermentables pre-fermentation such as in a dry grind alcohol production process that overcomes various of the aforementioned drawbacks.

SUMMARY

Embodiments of the present invention relate to improved systems and processes for adding pre-fermentation separated non-fermentables (e.g., fiber, germ/oil, and/or protein) to a post-fermentation stream, e.g., a dry grind alcohol and/or other biofuel or biochemical production process, that realize any number of process enhancements compared to typical processes. Incorporating the pre-fermentation separated non-fermentables to a post-fermentation stream provides the benefit of gaining fermentation time while being able to continue maximizing operation of the post-distillation equipment based on the original optimized processing conditions for streams including the non-fermentables.

In one embodiment, a process for adding pre-fermentation separated non-fermentables to a post-fermentation stream is provided that includes mixing grain particles with a liquid to produce a slurry having starch and non-fermentables, including fiber. Then, the slurry is subjected to liquefaction to convert the starch in the slurry to complex sugars and produce a liquefied stream including the complex sugars and the non-fermentables. After liquefaction but prior to fermentation of simple sugars resulting from conversion of the complex sugars, the non-fermentables are separated out to define a non-fermentables portion, including the fiber, and an aqueous solution including the complex and/or simple sugars. Then, the simple sugars are fermented to provide a fermented stream. Thereafter, the separated non-fermentables portion, including the fiber, are reincorporated back into the process into a post-fermentation stream. In one example, after liquefaction but prior to fermentation of simple sugars resulting from conversion of the complex sugars, the fiber of the non-fermentables is separated out to define a non-fermentables fiber portion and an aqueous solution including the complex and/or simple sugars, and the separated non-fermentables fiber portion is reincorporated back into the process into a post-fermentation stream.

In another embodiment, a process for adding pre-fermentation separated non-fermentables to a post-fermentation stream is provided that includes mixing corn grain particles with a liquid to produce a slurry having starch and non-fermentables, including fiber. Then, the slurry is subjected to liquefaction to convert the starch in the slurry to complex sugars and produce a liquefied stream including the complex sugars and the non-fermentables. The non-fermentables next are separated out from the liquefied stream to define a non-fermentables portion, including the fiber, and an aqueous solution including the complex sugars. The aqueous solution is subjected to saccharification to convert the complex sugars to simple sugars and the simple sugars fermented to provide a fermented stream. Thereafter, the separated non-fermentables portion, including the fiber, is reincorporated back into the process into a post-fermentation stream. In one example, the fiber of the non-fermentables is separated out from the liquefied stream to define a non-fermentables fiber portion and an aqueous solution including the complex sugars, and the separated non-fermentables fiber portion is reincorporated back into the process into a post-fermentation stream.

In yet another embodiment, a system for adding pre-fermentation separated non-fermentables to a post-fermentation stream is provided that includes a first apparatus that is configured to hold a slurry of grain particles and a liquid. The slurry has starch and non-fermentables, including fiber. A liquefaction system is situated after the first apparatus and is configured to receive the slurry. The liquefaction system converts the starch in the slurry to complex sugars and produces a liquefied stream including the complex sugars and the non-fermentables. A second apparatus is situated after the liquefaction system and is configured to receive and separate out the non-fermentables to define a non-fermentables portion, including the fiber, and an aqueous solution including the complex sugars and/or simple sugars resulting from conversion of the complex sugars. A fermenter is situated after the second apparatus and is configured to receive and ferment the simple sugars from conversion of the complex sugars to provide a fermented stream. The system is configured to reincorporate the separated non-fermentables portion, including the fiber, into a post-fermentation stream. In one example, the second apparatus is situated after the liquefaction system and configured to receive and separate out the fiber of the non-fermentables to define a non-fermentables fiber portion and an aqueous solution including the complex sugars and/or simple sugars resulting from conversion of the complex sugars, and the system is configured to reincorporate the separated non-fermentables fiber portion into a post-fermentation stream.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention.

DETAILED DESCRIPTION OF SPECIFIC EMBODIMENTS

Figure 1:
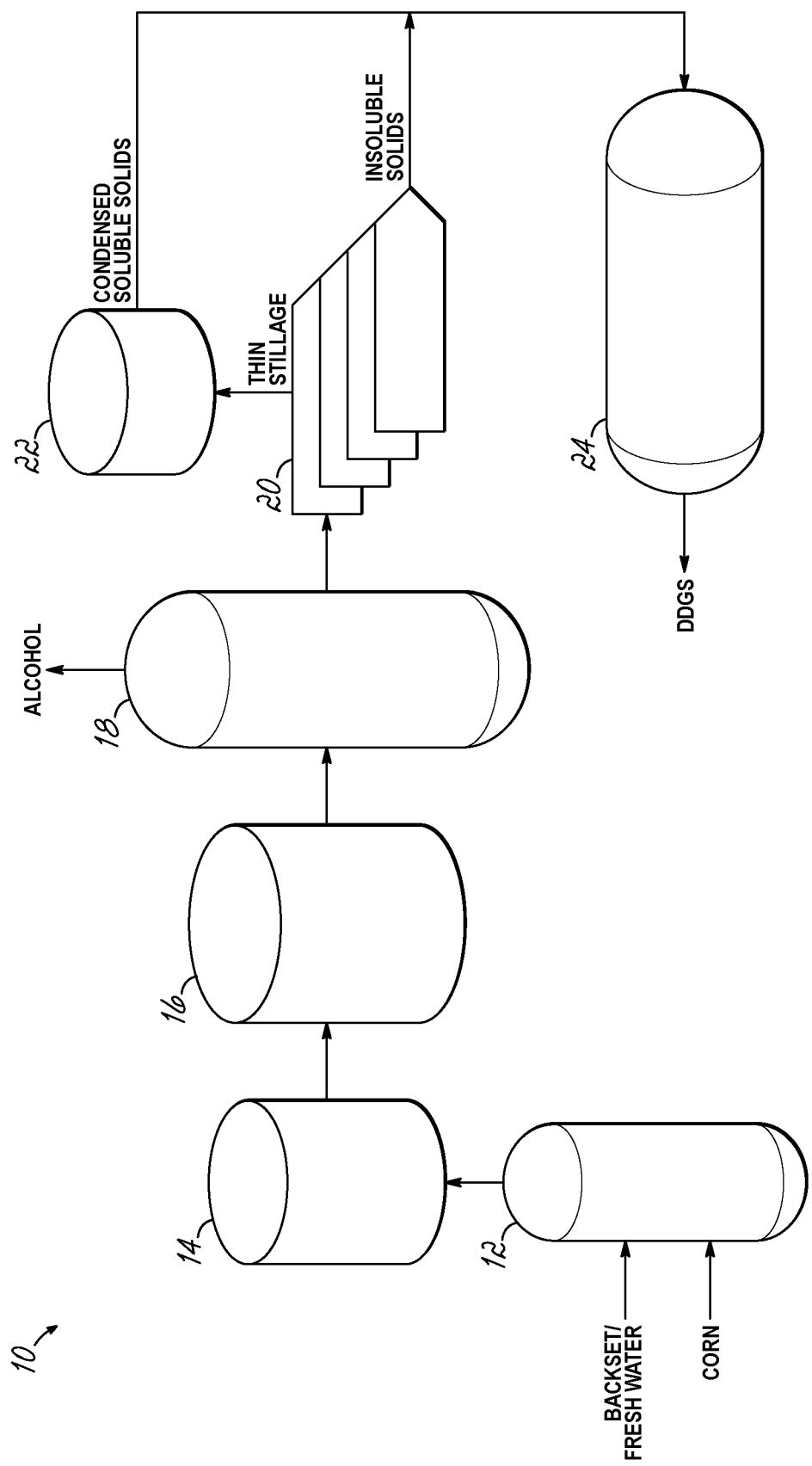
FIG. 1 is a flow diagram showing a typical dry grind alcohol production process.
Figure 2:
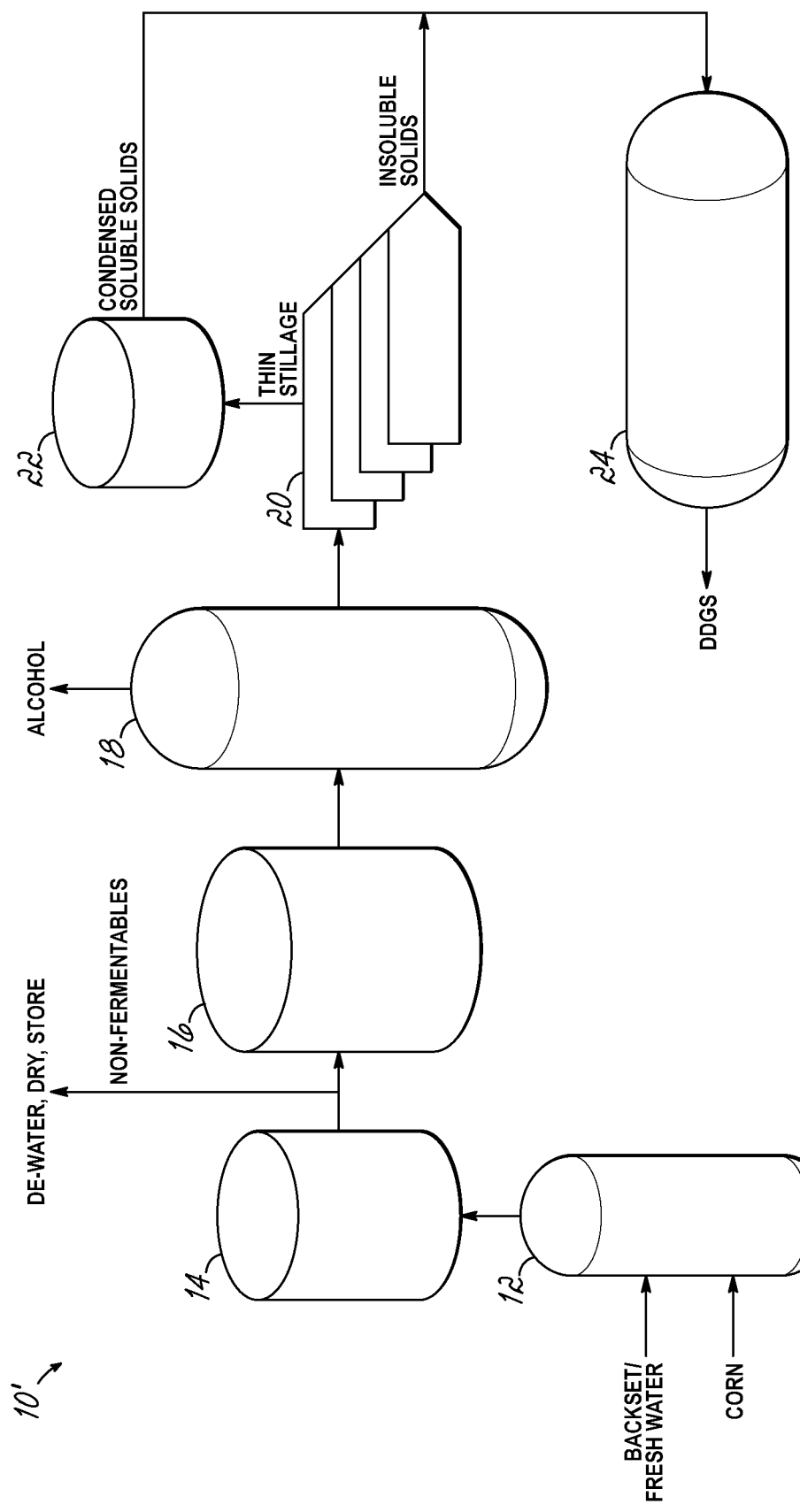
FIG. 2 is a flow diagram showing a typical dry grind alcohol production process with pre-fermentation separation and front end processing of non-fermentables.

FIGS. 1 and 2, which have been generally discussed above, illustrate flow diagrams of typical dry grind ethanol production processes without and with pre-fermentation separation and front end processing of non-fermentables, respectively, and are more fully discussed next.

With specific reference to FIG. 1, a typical corn dry milling process 10 begins with a traditional milling step (not shown) in which dried whole corn kernels are passed through hammer mills to grind them into meal or a fine powder including grain particles. The ground meal is mixed with water, such as backset and/or fresh water, to create a slurry at slurry tank 12, and a commercial enzyme such as alpha-amylase is added. In a cooking and liquefaction process 14, the slurry is typically pH adjusted and heated in a pressurized jet cooking process to solubilize the starch in the ground meal followed by liquefaction of the solubilized starch at which point additional alpha-amylase may be added. The alpha-amylase hydrolyzes the gelatinized starch into maltodextrins and oligosaccharides (i.e., complex sugars) and produces a liquefied mash or slurry. This can be followed by a simultaneous saccharification and fermentation step 16, each of which also may occur separately in desired systems. The saccharification and fermentation step 16 can include a further pH and temperature adjustment. With saccharification, the liquefied mash is cooled and a commercial enzyme, such as gluco-amylase, is added to hydrolyze the maltodextrins and short-chained oligosaccharides into simple sugars, such as single glucose sugar molecules. With fermentation, yeast (e.g., *Saccharomyces cerevisae*) can be used to metabolize the glucose sugars into ethanol and $CO_2$, such as in a fermenter whereat the saccharification may simultaneously occur. Other fermentation agents such as microbial, including bacterial such as clostridia, and the like can be utilized. Upon completion, the fermentation mash ("beer") may contain about 17% to 18% ethanol (volume/volume basis), plus soluble and insoluble solids from all the remaining grain components, including fiber, protein, minerals, and germ/oil, for example. Yeast can optionally be recycled in a yeast recycling step (not shown). In some instances, the $CO_2$ is recovered and sold as a commodity product.

Subsequent to the saccharification and fermentation step 16 is a distillation and dehydration step 18 in which the fermentation stream is pumped into distillation columns where it is boiled to vaporize the ethanol. The ethanol vapor after exiting the top of the distillation column is condensed and liquid alcohol (in this instance, ethanol) is about 95% purity (190 proof). The 190 proof ethanol can then go through a molecular sieve dehydration column or a membrane separation unit or similar dehydration system, which removes the remaining residual water from the ethanol, to yield a final product of essentially 100% ethanol (199.5 proof).

Finally, a centrifugation step 20 subjects the residuals or whole stillage leftover from the distillation step 18 whereat a series of decanter centrifuges separate the insoluble solids portion or "wet cake", which includes fiber, from the remaining liquid portion or "thin stillage" portion, which includes protein, amino acids, oil, etc. Next, the thin stillage portion enters evaporators 22 in an evaporation step to boil away moisture thereby leaving a thick syrup, which contains the soluble (dissolved) solids as well as protein and oil. This concentrated syrup is typically referred to as corn condensed distillers soluble and is mixed with the centrifuged wet cake then sold to beef and dairy feedlots as distillers wet grain with solubles (DWGS). The wet cake and concentrated syrup mixture may be further dried in a drying step 24 and sold as distillers dried grain with solubles (DDGS) to dairy and beef feedlots and/or the monogastric markets. The distillers grains with solubles co-product provides a critical secondary revenue stream that offsets a portion of the overall ethanol production cost.

With reference now to FIG. 2, another typical or conventional dry milling process 10' is shown that is similar to the typical corn dry milling process 10 of FIG. 1, with the exception that non-fermentables, including fiber, germ/oil, protein, and/or other non-fermentable component(s), can be separated from the liquefied slurry before fermentation such as directly after the cooking and liquefaction process 14. These separated non-fermentables are sent to front end dewatering and/or drying processes and eventually storage or sold as is. And the remainder of the aqueous portion of the slurry is subjected to the rest of the typical process, as discussed above with respect to FIG. 1, except that the residuals from the distillation step 18 include primarily fine or low coarse solids at centrifugation step 20, and not the traditional whole stillage leftovers because at least a portion of the non-fermentables have been separated out at the front end of the process. The residual solids then are subjected to the series of decanter centrifuges at centrifuge step 20 to separate the remaining insoluble fine solids portion from the liquid portion or "thin stillage" portion, with each portion being further processed as above described.

Figure 3:
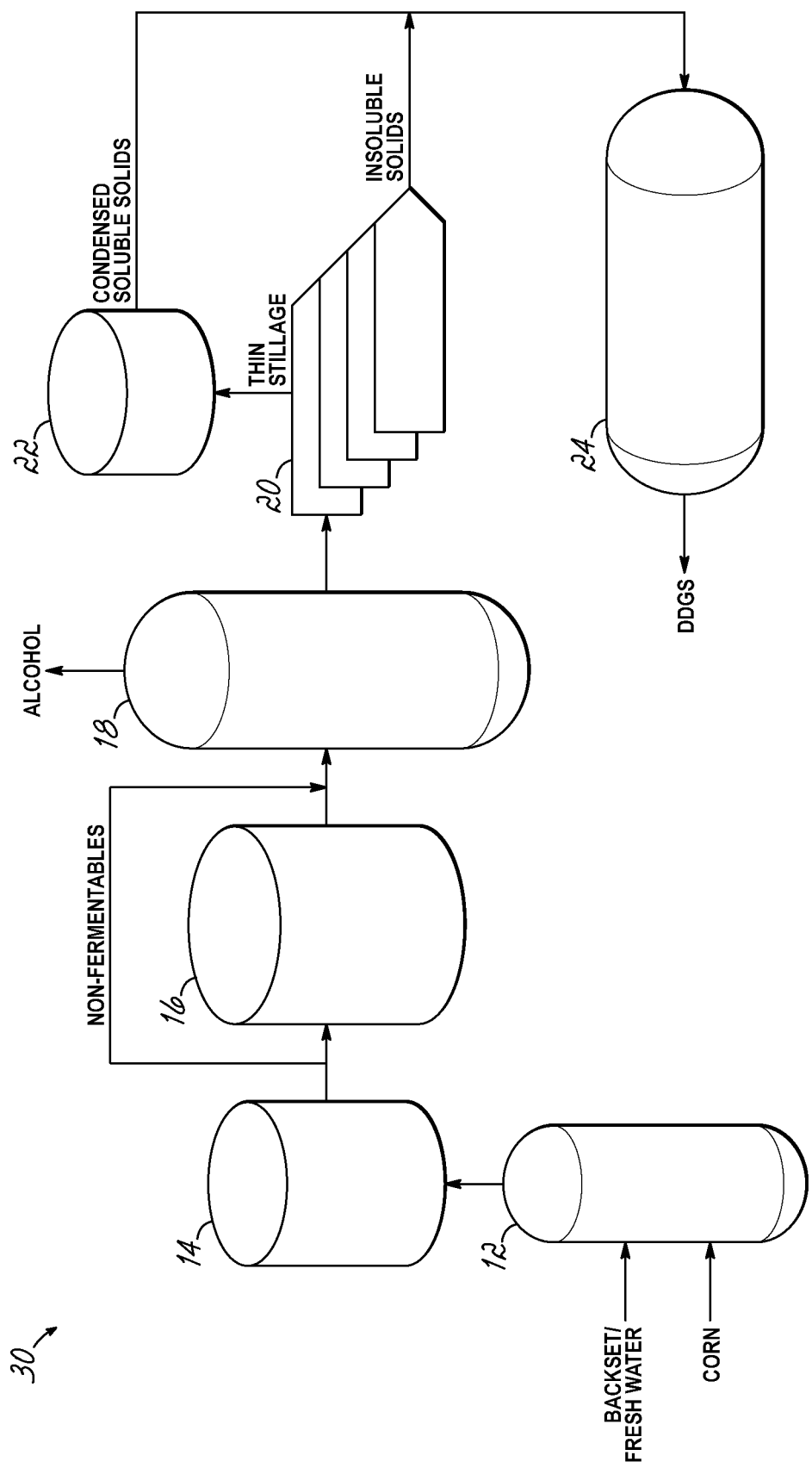
FIG. 3 is a flow diagram showing a system and process for adding pre-fermentation separated non-fermentables to a post-fermentation stream in accordance with an embodiment of the invention.
Figure 4:
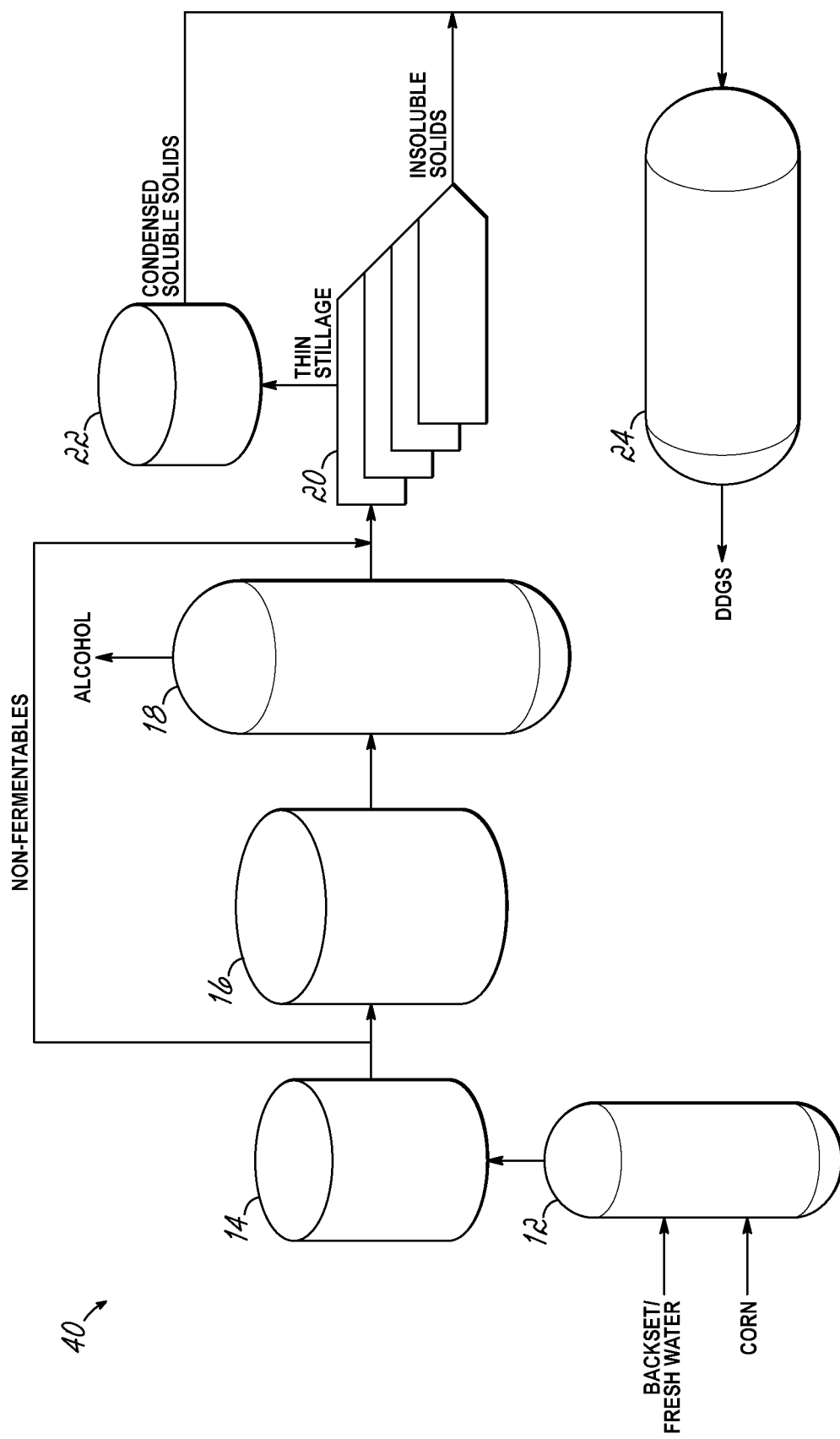
FIG. 4 is a flow diagram showing a system and process for adding pre-fermentation separated non-fermentables to a post-fermentation stream in accordance with another embodiment of the invention.

In accordance now with the present invention, FIGS. 3 and 4 illustrate various embodiments of a system and process for adding pre-fermentation separated non-fermentables (e.g. fiber, germ/oil, and/or protein) to a post-fermentation stream. The systems and processes of the present invention, which are discussed in detail hereinbelow, can remove desirable amounts of non-fermentables pre-fermentation and recombine the same to a post-fermentation (or post-distillation stream) to realize any number of process enhancements. In particular, it can be advantageous to re-introduce the separated non-fermentables, which may be mainly fiber, directly after fermentation (FIG. 3) or, in some cases, after fermentation and distillation (FIG. 4), i.e., directly after distillation. Ethanol plants generally operate either pressure or vacuum distillation systems to flash off the alcohol product prior to condensing it. There are merits to both designs, with some limitations to the pressure distillation systems when operating with low insoluble solids/non-fermentables content in the system. Therefore, while there are recognized benefits with removing the non-fermentables prior to fermentation, it is advantageous to return some or all of the non-fermentables components to the processing stream directly after fermentation or, in some cases, not until after distillation.

With specific reference to FIG. 3, this figure schematically illustrates an embodiment of a system and process, collectively numeral 30, for separating non-fermentables, e.g., fiber, germ/oil, protein, and/or other non-fermentable components, pre-fermentation and incorporating the separated non-fermentables in the post-fermentation steam prior to distillation 18 during a typical corn dry-milling process 10, like that just described in FIG. 1. While a typical corn dry-milling process is modified here at FIG. 3, it should be understood that any corn or similar or other grain dry milling process may be modified/utilized with the same or similar results. In one example, the non-fermentables portion may be or may be mainly fiber, protein, and/or germ/oil. In another example, the non-fermentables portion may be or may be mainly fiber and/or protein.

With continuing reference now to FIG. 3, after the cooking and liquefaction process 14 but prior to fermentation, the liquefied stream can be separated into a non-fermentables portion, including fiber, protein, and/or germ/oil, and an aqueous portion, including complex sugars such as maltodextrins and oligosaccharides (i.e., starch components), which eventually will be subjected to fermentation. Separating the non-fermentables portion pre-fermentation or pre-saccharification can provide the benefit of gaining fermentation time and efficiency. In another example, it should be understood that the non-fermentables portion may be separated out after saccharification but prior to fermentation in a system that employs non-simultaneous saccharification and fermentation to provide an aqueous solution, including simple sugars, and then reintroducing the separated non-fermentables portion back into the system and process 30, as below discussed. In one example, the separated non-fermentables portion may be or may be mainly fiber, protein, or germ/oil and the aqueous portion may be mainly complex and/or simple sugars. In another example, the separated non-fermentables portion may be or may be mainly fiber and/or protein, such as to define a non-fermentables fiber and/or protein portion.

Concerning separating out the non-fermentables portion, the liquefied (or saccharified) stream can be subjected to a paddle screen, for example, to filter or separate out the non-fermentables portion from the liquefied (or saccharified) stream to provide the aqueous portion. The paddles screen can be provided with washing capabilities so that water (or other suitable liquid), along with the liquefied stream, can be supplied to, or prior to, the paddle screen. The additional water, such as fresh water, can allows for easier separation of the liquefied stream into its non-fermentables portion and aqueous portion.

In one example, the paddle screen can include screen openings of no greater than about 500 microns. In another example, the paddle screen can include openings therein of no greater than about 400 microns. In yet another example, the openings therein are no greater than about 300 microns. In yet another example, the paddle screen can include openings therein of no greater than about 150 microns. And in yet another example, the paddle screen can include openings therein of no greater than about 50 microns. It should be understood that these values are exemplary and that those of ordinary skill in the art will recognize how to determine the size of the openings to achieve the desired separation. In one example, the paddle screen is a standard type paddle screen as is known in the art. One such suitable paddle screen is the FQ-PS32 available from Fluid-Quip, Inc. of Springfield, Ohio. It should be understood that the paddle screen 34 may be replaced with other types of pre-concentration or separation type devices, e.g., a standard pressure screen, filter press, or centrifuge, such as a conic centrifuge, which can perform the desired filtration/separation or preconcentration function. One such suitable pressure screen is the PS-Triple available from Fluid-Quip, Inc. of Springfield, Ohio. It should be understood that a plurality of filtration/separation devices may be situated in-line, either parallel and/or in series, and utilized for filtering out the non-fermentables portion. Also, although the liquefied stream is discussed as being separated into two portions, the stream could be separated into three or more portions and any non-fermentables and/or aqueous portions recombined, as needed/desired, to define the non-fermentables portion and/or aqueous portion.

With further reference to FIG. 3, the remaining aqueous portion can be subjected to saccharification and fermentation at the saccharification and fermentation step 16 to produce a fermented stream. After or post-fermentation of the aqueous portion, the separated out non-fermentables portion can be incorporated back into the process 30 such as directly into the fermented stream. Incorporation or reincorporation of the separated out non-fermentables portion can occur specifically at the beer well or directly into the beer feed stream pre or post the typical reclaim heat exchanger. That is, reincorporation can occur post-fermentation but prior to the distillation column/distillation at distillation step 18.

In one embodiment, the distillation step 18 can include a pressure distillation system. In a pressure distillation system, the distillation trays traditionally get 'scrubbed' by larger or coarser fiber being forced across the distillation trays. Thus, it can be advantageous to send the non-fermentables, particularly fiber, to the beer well or directly into to the beer feed stream, i.e., into the fermented stream, so as to re-introduce separated out fiber prior to distillation thereby keeping the distillation trays clean and avoiding fouling. To that end, this process and system 30 achieves the benefit of removing the non-fermentables from fermentation, while allowing the non-fermentables, e.g., fiber, to help scrub the distillation trays to keep them clean so as to extend operating life and improve distillation efficiency by having cleaner distillation trays. Additional benefits include avoiding the additional front end processing equipment to dewater and/or dry fiber that is traditionally recovered pre-fermentation and also continuing to operate the post-fermentation equipment as optimized for original operating conditions. The rest of the system and process 30 after distillation is as discussed above with FIG. 1.

With reference now to FIG. 4, this figure schematically illustrates another embodiment of a system and process, collectively numeral 40, for separating non-fermentables pre-fermentation and incorporating the separated non-fermentables in a post-fermentation steam like as shown in FIG. 3, except that the separated non-fermentable portion is re-incorporated into a stream post-distillation, e.g., directly after distillation step 18, rather than directly after fermentation.

With continuing reference now to FIG. 4, as shown, after the cooking and liquefaction process 14 but prior to fermentation, the liquefied stream can be separated into a non-fermentables portion, including fiber, protein, and/or germ/oil, and an aqueous portion, including complex sugars such as maltodextrins and oligosaccharides (i.e., starch components), which eventually will be subjected to fermentation. Again, it should be understood that the non-fermentables portion may be separated out after saccharification but prior to fermentation in a system that employs non-simultaneous saccharification and fermentation to provide an aqueous solution including simple sugars, and then reintroducing the separated non-fermentables portion back into the system and process 40, as below discussed. In one example, the separated non-fermentables portion may be or may be mainly fiber, protein, and/or germ/oil and the aqueous portion may be mainly complex and/or simple sugars. In another example, the separated non-fermentables portion may be or may be mainly fiber and/or protein, such as to define a non-fermentables fiber and/or protein portion. As discussed above concerning FIG. 3, separation of the non-fermentables can occur via a paddle screen or other like filtration/separation device, including pressure screens and centrifuges.

With further reference to FIG. 4, after the non-fermentable portion has been separated out, as is shown, the remaining aqueous portion can be subjected to saccharification and fermentation at the saccharification and fermentation step 16 to produce a fermented stream. That fermented stream is subjected to distillation at distillation step 18 that vaporizes the ethanol leaving the residuals or whole stillage. The separated out non-fermentables portion can be incorporated back or reincorporated into a post-fermentation stream of the process 40 and, more specifically, reincorporated into the residuals stream directly after the distillation step 18 so as to define the whole stillage stream.

In one embodiment, the distillation step 18 can include a vacuum distillation system. If a plant is operating vacuum distillation, the distillation trays tend not to foul as easily and the non-fermentables, particularly fiber, are not necessary to help 'scrub' the distillation trays clean as with pressure distillation. Thus, keeping the fiber component out of both fermentation and distillation can be beneficial because there is less mass traveling through the distillation system resulting in a reduced energy/heating requirement. However, it can still be advantageous to add the pre-fermentation separated non-fermentables portion back into the "whole stillage" or residuals stream after distillation. This provides the benefits of continuing to operate the post-distillation equipment, such as the stillage decanters at centrifuge step 20, thin stillage evaporator(s) 22, and dryer(s) at drying step 24 as maximally optimized for original operating conditions. It also eliminates the additional equipment and operating costs of front end de-watering, drying, storing, and handling of the non-fermentables traditionally removed and isolated pre-fermentation. The rest of the system and process 40 after distillation is as discussed above with FIG. 1.

Although fiber can be the preferred non-fermentable corn component, the system and process 30, 40 can achieve benefits from the various non-fermentables that may be removed prior to fermentation, including, but not limited to germ, coarse fiber, fine fiber, protein, oil, minerals, etc., and the like. In addition, although corn is the feedstock discussed throughout, similar systems have been utilized for other grain based alcohol and biofuel/biochemical processes and the benefits of returning non-fermentable solids to the process stream after fermentation and/or distillation can achieve similar benefits. For example, virtually any type of grain whether whole and fractionated or any carbohydrate source, including, but not limited to, wheat, barley, sorghum, rye, rice, oats, sugar cane, tapioca, triticale, potato, cassava, or the like, as well as other biomass products is contemplated here.

In addition, other options for the simple sugar stream, aside from fermentation, can include converting the glucose to other chemical compounds, including other simple or even complex sugars, acids, alcohols, and the like (e.g., fructose, propanol, isobutanol, citric acid, succinic acid, or lactic acid) by means and methods known in the art, which can be used as or in feed/food products, pharmaceuticals, nutraceuticals, and the like. That is, fermentation (and optionally other back end steps/processes, including distillation, etc.) can be wholly replaced with other chemical and biological conversion processes known in the art that utilize yeast, bacteria, microbes, or the like to convert glucose to other biofuels and/or biochemicals. In such other processes, the simple sugars in the simple sugar stream can be converted to form other chemical compounds via a biofuel and/or biochemical device, e.g., a reactor, which may be a fermenter, to define a converted simple sugar stream, i.e., another chemical compound. In turn, the non-fermentables discussed above can define non-convertables that can be separated out prior to conversion of the simple sugars, with the pre-conversion separated non-convertables being reintroduced post-conversion, like as discussed above in FIGS. 3 and 4 with respect to fermentation.

In addition, in another embodiment, it should be understood that all or a portion of the separated non-fermentables (or non-convertables) can be used in or for other processing and/or feed uses instead of being solely reintroduced post fermentation or distillation (or post-conversion). In one example, non-fermentable fiber can be transported to a remote site for further processing, such as anaerobic or aerobic digestion, conversion to C5 and C6 sugar molecules for biofuel, or biochemical conversion processes. Also, the separated non-fermentable stream may be further processed prior to being reintroduced back to the downstream process to enhance the streams functional characteristics. In another embodiment, all or a portion of the separated non-fermentables (or non-convertables), such as non-fermentable fiber, can be reintroduced after evaporation step 22 or centrifugation step 20, but prior to drying step 24, for example, by recombining the same with the condensed soluble solids and/or the insoluble solids streams.

Processing aids can be added to the separated stream such as to improve the distillation process and/or pH modified such as to prevent proteins from plating out or sticking to the distillation column trays. Other processing or modification to the separated stream can include changing ion strength, for example. In addition, it should be understood that the separated non-fermentables (or non-convertables) portion may be further separated or treated to provide two or more non-fermentable steams and all or a portion of one or more of those new streams processed and/or reintroduced downstream, or not at all, as discussed above. In one example, the non-fermentables portion may be or may be mainly fiber, protein, and/or germ/oil, such that protein or fiber, for example, may be subsequently separated out therefrom and further processed and/or reintroduced downstream, or not at all and used in or for cellulosic fiber conversion to sugars, protein animal feeds, chemical conversion to other biofuels and/or biochemicals, etc. as known in the art.

Accordingly, an improved system and process 30, 40 for adding pre-conversion separated non-convertables, such as pre-fermentation separated non-fermentables, to a post conversion stream, such as a post fermentation stream, in a dry grind alcohol and/or other biofuel or biochemical production process, is provided that realizes any number of process enhancements, which are improvements over typical processes and others.

While the present invention has been illustrated by a description of various embodiments and while these embodiments have been described in considerable detail, it is not the intention of the applicant to restrict or in any way limit the scope of appended claims to such detail. Additional advantages and modifications will readily appear to those skilled in the art. Thus, the invention in its broader aspects is therefore not limited to the specific details, representative systems and processes, and any illustrative examples shown and described. Accordingly, departures may be made from such details without departing from the spirit or scope of applicant's general inventive concept.

What is claimed is:

1. A process for adding pre-fermentation separated non-fermentables to a post-fermentation stream, the process comprising:
    mixing grain particles with a liquid to produce a slurry having starch and non-fermentables, including coarse fiber;
    subjecting the slurry to liquefaction to convert the starch in the slurry to complex sugars and produce a liquefied stream including the complex sugars and the non-fermentables;
    after liquefaction but prior to fermentation of simple sugars from conversion of the complex sugars, separating out at least a portion of the non-fermentables to define a non-fermentables portion, including the coarse fiber, and an aqueous solution including the complex and/or simple sugars;
    thereafter, fermenting the simple sugars to provide a fermented stream;
    reincorporating the separated non-fermentables portion, including the coarse fiber, back into the process into a post-fermentation stream including into either the fermented stream directly after fermenting the simple sugars or into a residuals stream directly after distillation of the fermented stream; and
    thereafter, separating the post-fermentation stream, which includes the reincorporated non-fermentables portion and thin stillage, into a thin stillage portion and a wet cake portion, which includes the reincorporated non-fermentables portion, including the coarse fiber.

2. The process of claim 1 wherein fermenting the simple sugars to provide a fermented stream comprises fermenting the simple sugars to provide fructose, propanol, isobutanol, citric acid, succinic acid, or lactic acid.

3. The process of claim 1 wherein the grain particles are corn grain particles and the process is a dry grind corn milling process.

4. The process of claim 1 wherein the separated non-fermentables portion, including the coarse fiber, is reincorporated back into the process into the fermented stream directly after fermenting the simple sugars.

5. The process of claim 1 wherein the separated non-fermentables portion, including the coarse fiber, is reincorporated back into the process into the residuals stream directly after distillation of the fermented stream.

6. The process of claim 1 wherein after liquefaction but prior to fermentation of simple sugars resulting from conversion of the complex sugars comprises directly after liquefaction but prior to saccharification of the complex sugars, separating out the non-fermentables from the liquefied stream to define a non-fermentables portion, including the coarse fiber, and an aqueous solution, including the complex sugars, and subjecting the aqueous solution to saccharification to convert the complex sugars to simple sugars then fermenting the simple sugars provide the fermented stream.

7. The process of claim 1 further comprising subjecting the liquefied stream to saccharification to convert the complex sugars to simple sugars, and wherein after liquefaction but prior to fermentation of simple sugars resulting from conversion of the complex sugars comprises after saccharification but prior to fermentation of the simple sugars, separating out the non-fermentables to define a non-fermentables portion, including the coarse fiber, and an aqueous solution including the simple sugars.

8. The process of claim 1 further comprising vacuum distilling the fermented stream to produce alcohol and provide a residuals stream, and reincorporating the separated non-fermentables portion, including the coarse fiber, back into the residuals stream from distillation.

9. The process of claim 1 further comprising pressure distilling the fermented stream to produce alcohol and provide a residuals stream, and reincorporating the separated non-fermentables portion, including the coarse fiber, back into the fermented stream prior to distillation.

10. The process of claim 1 wherein after liquefaction but prior to fermentation of simple sugars resulting from conversion of the complex sugars, separating out the coarse fiber of the non-fermentables to define a non-fermentables coarse fiber portion and an aqueous solution including the complex and/or simple sugars, and reincorporating the separated non-fermentables coarse fiber portion back into the process into a post-fermentation stream.

11. A process for adding pre-fermentation separated non-fermentables to a post-fermentation stream, the process comprising:
    mixing corn grain particles with a liquid to produce a slurry having starch and non-fermentables, including coarse fiber;
    subjecting the slurry to liquefaction to convert the starch in the slurry to complex sugars and produce a liquefied stream including the complex sugars and the non-fermentables;
    separating out at least a portion of the non-fermentables from the liquefied stream to define a non-fermentables portion, including the coarse fiber, and an aqueous solution including the complex sugars;
    subjecting the aqueous solution to saccharification to convert the complex sugars to simple sugars;
    thereafter, fermenting the simple sugars to provide a fermented stream;
    reincorporating the separated non-fermentables portion, including the coarse fiber, back into the process into a post-fermentation stream including into either the fermented stream directly after fermenting the simple sugars or into a residuals stream directly after distillation of the fermented stream; and
    thereafter, separating the post-fermentation stream, which includes the reincorporated non-fermentables portion and thin stillage, into a thin stillage portion and a wet cake portion, which includes the reincorporated non-fermentables portion, including the coarse fiber.

12. The process of claim 11 wherein, after subjecting the slurry to liquefaction to convert the starch in the slurry to complex sugars and produce the liquefied stream including the complex sugars and the non-fermentables, separating out the coarse fiber of the non-fermentables from the liquefied stream to define a non-fermentables coarse fiber portion and an aqueous solution including the complex sugars, and reincorporating the separated non-fermentables coarse fiber portion back into the process into a post-fermentation stream.

* * * * *

UNITED STATES PATENT AND TRADEMARK OFFICE
CERTIFICATE OF CORRECTION

PATENT NO. : 10,995,346 B2  
APPLICATION NO. : 15/649806  
DATED : May 4, 2021  
INVENTOR(S) : Michael Franko et al.

Page 1 of 1

It is certified that error appears in the above-identified patent and that said Letters Patent is hereby corrected as shown below:

In the Specification

Column 1, Line 6-7, reads "The present invention relates generally to corn dry milling, and more specifically, to a" should be --The present invention relates generally to corn dry milling and, more specifically, to a--.

Column 5, Line 20, reads "non-fermentables in the post-fermentation steam prior to" should be --non-fermentables in the post-fermentation stream prior to--.

Column 5, Line 61, reads "additional water, such as fresh water, can allows for easier" should be --additional water, such as fresh water, can allow for easier--.

Column 6, Lines 45-47, reads "it can be advantageous to send the non-fermentables, particularly fiber, to the beer well or directly into to the beer fed stream" should be --it can be advantageous to send the non-fermentables, particularly fiber, to the beer well or directly into the beer feed stream,--.

Column 6, Lines 65-66, reads "pre-fermentation and incorporating the separated non-fermentables in a post-fermentation steam like as shown in" should be --pre-fermentation and incorporating the separated non-fermentables in a post-fermentation stream like as shown in--.

Column 8, Line 60, reads "non-fermentable steams and all or a" should be --non-fermentable streams and all of a--.

In the Claims

Column 10, Lines 9-11, Claim 6, reads "saccharification to convert the complex sugars to simple sugars then fermenting the simple sugars provide the fermented stream." should be --saccharification to convert the complex sugars to simple sugars then fermenting the simple sugars to provide the fermented stream.--.

Signed and Sealed this  
Twentieth Day of July, 2021

Drew Hirshfeld  
*Performing the Functions and Duties of the*  
*Under Secretary of Commerce for Intellectual Property and*  
*Director of the United States Patent and Trademark Office*